United States Patent
Yamashita et al.

(10) Patent No.: US 11,259,713 B2
(45) Date of Patent: Mar. 1, 2022

(54) BIOLOGICAL INFORMATION MEASUREMENT DEVICE, AND BIOLOGICAL INFORMATION MEASUREMENT SUPPORT METHOD

(71) Applicant: OMRON HEALTHCARE CO., LTD., Kyoto (JP)

(72) Inventors: Shingo Yamashita, Muko (JP); Naoki Maeda, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 430 days.

(21) Appl. No.: 16/223,667

(22) Filed: Dec. 18, 2018

(65) Prior Publication Data

US 2019/0117092 A1    Apr. 25, 2019

Related U.S. Application Data

(63) Continuation of application No. PCT/JP2017/022719, filed on Jun. 20, 2017.

(30) Foreign Application Priority Data

Jun. 24, 2016  (JP) .............................. JP2016-125938

(51) Int. Cl.
    *A61B 5/0255*      (2006.01)
    *A61B 5/02*      (2006.01)
    *A61B 5/00*      (2006.01)

(52) U.S. Cl.
CPC .............. *A61B 5/0255* (2013.01); *A61B 5/02* (2013.01); *A61B 5/6843* (2013.01); *A61B 5/7221* (2013.01); *A61B 2562/0247* (2013.01)

(58) Field of Classification Search
CPC ....... A61B 5/0255; A61B 5/02; A61B 5/6843; A61B 5/7221; A61B 2562/0247
See application file for complete search history.

(56) References Cited

U.S. PATENT DOCUMENTS

2008/0242956 A1* 10/2008 Suzuki ................ A61B 5/4035
                                                              600/301
2009/0156948 A1     6/2009 Shimizu et al.
(Continued)

FOREIGN PATENT DOCUMENTS

CN        101272731       9/2008
CN        104053396       9/2014
(Continued)

OTHER PUBLICATIONS

International Search Report dated Aug. 22, 2017 in International (PCT) Application No. PCT/JP2017/022719 with English translation.

(Continued)

*Primary Examiner* — Devin B Henson
*Assistant Examiner* — Joseph A Tombers
(74) *Attorney, Agent, or Firm* — Wenderoth, Lind & Ponack, L.L.P.

(57) ABSTRACT

A biological information measurement device includes: a pulse wave detection unit that continuously detects pulse waves from a living body; a biological information calculation unit that calculates biological information based on pulse waves detected by the pulse wave detection unit and stores, in a storage medium, biological information calculation results information including said biological information; a storage control unit that stores, in the storage medium, pulse wave detection results information by the pulse wave detection unit in order to calculate biological information included in biological information calculation results information; a measurement efficiency information generation unit that generates measurement efficiency information indicating measurement efficiency for biological information included in biological information calculation results information, generating same based on the biological (Continued)

information calculation results information and pulse wave detection results information; and a control unit that notifies when the measurement efficiency information fulfills a condition.

12 Claims, 4 Drawing Sheets

(56) References Cited

U.S. PATENT DOCUMENTS

| | | | |
|---|---|---|---|
| 2010/0228139 A1 | 9/2010 | Nanba et al. | |
| 2011/0144918 A1 | 6/2011 | Inoue | |
| 2012/0203119 A1* | 8/2012 | Yamashita | A61B 5/6824 600/490 |
| 2013/0006123 A1 | 1/2013 | Aoshima | |
| 2014/0313052 A1 | 10/2014 | Yarger et al. | |
| 2014/0379273 A1 | 12/2014 | Petisce et al. | |
| 2015/0216458 A1 | 8/2015 | Kasahara et al. | |
| 2016/0259905 A1* | 9/2016 | Park | G16H 40/63 |
| 2018/0338726 A1 | 11/2018 | Yarger et al. | |

FOREIGN PATENT DOCUMENTS

| | | |
|---|---|---|
| CN | 104814745 | 8/2015 |
| JP | 11-004826 | 1/1999 |
| JP | 2000-139861 | 5/2000 |
| JP | 2007-215722 | 8/2007 |
| JP | 2008-237574 | 10/2008 |
| JP | 2010-88576 | 4/2010 |
| JP | 2010-207347 | 9/2010 |
| JP | 2011-92512 | 5/2011 |
| JP | 2012-183139 | 9/2012 |
| JP | 2012-183215 | 9/2012 |
| JP | 2016-052589 | 4/2016 |
| WO | 2013/038296 | 3/2013 |

OTHER PUBLICATIONS

Written Opinion of the International Searching Authority dated Aug. 22, 2017 in International (PCT) Application No. PCT/JP2017/022719.

International Preliminary Examination Report dated May 18, 2018 in International (PCT) Application No. PCT/JP2017/022719.

First Office Action dated Dec. 11, 2020 in corresponding Chinese Patent Application No. 201780037919.X, with English Translation.

* cited by examiner

| PULSE WAVE DETECTION DATE AND TIME | PULSE WAVE INFORMATION | BIOLOGICAL INFORMATION | MEASUREMENT FLAG |
|---|---|---|---|
| **** | **** | **** | 0 |
| **** | **** | **** | 0 |
| **** | **** | **** | 0 |
| **** | **** | — | 1 |
| **** | **** | — | 1 |
| **** | **** | — | 1 |
| **** | **** | — | 1 |
| **** | **** | **** | 0 |
| **** | **** | **** | 0 |
| **** | **** | **** | 0 |
| **** | **** | **** | 0 |
| **** | **** | **** | 0 |
| **** | **** | **** | 0 |
| ⋮ | ⋮ | ⋮ | ⋮ |

FIG. 4

BIOLOGICAL INFORMATION MEASUREMENT DEVICE, AND BIOLOGICAL INFORMATION MEASUREMENT SUPPORT METHOD

CROSS REFERENCE TO RELATED APPLICATIONS

This application is a continuation of PCT application No. PCT/JP2017/022719, which was filed on Jun. 20, 2017 based on Japanese Patent Application (No. 2016-125938) filed on Jun. 24, 2016, the contents of which are incorporated herein by reference.

BACKGROUND OF THE INVENTION

1. Field of the Invention

The present invention relates to a biological information measurement device, a biological information measurement support method and a biological information measurement support program.

2. Description of the Related Art

In general, the biological information necessary for in vivo diagnosis such as blood pressure information, pulse information, heartbeat information and the like largely changes in the day. For this reason, the biological information is continuously measured and recorded from a measurement subject for diagnosis and the like.

As a device configured to continuously measure the biological information, a device configured to detect a pulse wave every one pulse (a time period for which the heart beats one time) and to calculate and store the biological information in a unit of one pulse based on the detected pulse wave has been known. Also, a biological information measurement device configured to display an outline of the measured biological information or a reliability rate so as to inform a user of a measurement result and to support doctor's determination for taking a next action has been suggested (refer to Patent Documents 1 and 2).

Patent Document 1 discloses a biological information measurement device configured to continuously measure blood pressure information more than once by an oscillometric method and to display a reliability rate indicative of reliability of each of the measured blood pressure information after the multiple measurements of the blood pressure information are over. A doctor makes a diagnosis based on the other blood pressure information except the blood pressure information having a low reliability rate, based on the displayed reliability rates, thereby increasing the accuracy of the diagnosis.

Patent Document 2 discloses an activity meter having a heart rate measuring function and configured to display a trend graph of the heart rates at an end of measurement. A user of the activity meter can check activity situations of the user by seeing the trend graph and utilize the trend graph for exercise management, physical condition management and the like.

CITATION LIST

Patent Document

Patent Document 1: JP-A-2010-88576
Patent Document 2: JP-A-2007-215722

SUMMARY OF THE INVENTION

A biological information measurement device of the present invention includes a pulse wave detection unit configured to continuously detect a pulse wave from a living body, a biological information calculation unit configured to calculate and store biological information based on the pulse wave detected by the pulse wave detection unit in a storage medium, a storage control unit configured to store, in the storage medium, pulse wave detection result information indicative of a result of pulse wave detection processing executed by the pulse wave detection unit so as to calculate the biological information, a measurement efficiency information generation unit configured to generate measurement efficiency information indicative of a measurement efficiency of the biological information stored in the storage medium, based on biological information calculation result information indicative of a calculation result of the biological information made by the biological information calculation unit and the pulse wave detection result information, and a control unit configured to, when the measurement efficiency information satisfies a predetermined condition, execute a predetermined control.

A biological information measurement support method of the present invention includes a biological information calculation step of calculating biological information based on a pulse wave detected by a pulse wave detection unit configured to continuously detect the pulse wave from a living body and storing, as information indicative of a calculation result of the biological information, biological information calculation result information including at least the biological information in a storage medium, a storage control step of storing, in the storage medium, pulse wave detection result information indicative of a result of pulse wave detection processing executed by the pulse wave detection unit so as to calculate the biological information to be included in the biological information calculation result information, a measurement efficiency information generation step of generating measurement efficiency information indicative of a measurement efficiency of the biological information based on the biological information calculation result information and the pulse wave detection result information, and a control step of, when the measurement efficiency information satisfies a predetermined condition, executing a predetermined control.

A biological information measurement support program of the present invention is configured to enable a computer to execute a biological information calculation step of calculating biological information based on a pulse wave detected by a pulse wave detection unit configured to continuously detect the pulse wave from a living body and storing, as information indicative of a calculation result of the biological information, biological information calculation result information including at least the biological information in a storage medium, a storage control step of storing, in the storage medium, pulse wave detection result information indicative of a result of pulse wave detection processing executed by the pulse wave detection unit so as to calculate the biological information to be included in the biological information calculation result information, a measurement efficiency information generation step of generating measurement efficiency information indicative of a measurement efficiency of the biological information based on the biological information calculation result information and the pulse wave detection result information, and a control step of, when the measurement efficiency information satisfies a predetermined condition, executing a predetermined control.

DETAILED DESCRIPTION OF THE EXEMPLARY EMBODIMENTS

The biological information measurement device configured to measure the biological information in a unit of one pulse is used with being worn on a body of the measurement subject for a long time. For this reason, when the body motion of the measurement subject largely changes, the pulse wave may deviate from a correct value.

A technology of detecting the body motion and correcting the biological information based on the detected body motion has been known. However, it is not easy to correct the biological information that is being measured while the body motion changes. Therefore, it is advantageous from the aspect of cost to treat the measurement of the biological information as failure or unmeasurable for a time period in which the body motion largely changes.

Thus, in the biological information measurement device that is assumed to be used with being worn on the living body for a long time, it is considered to determine a measurement success and a measurement failure of the biological information in the device and to store only a successfully measured measurement result.

However, the determination is made in the device, so that the measurement subject cannot know the same. For this reason, if the measurement subject wears the biological information measurement device, assumes that the biological information is always measured successfully and has a regular life, a time period in which the measurement of the biological information actually fails may occur in many cases. Therefore, the significance of measuring the biological information with wearing the device for a long time may disappear. Patent Documents 1 and 2 do not consider the situations.

The present invention has been made in view of the above situations, and an object thereof is to provide a biological information measurement device, a biological information measurement support method, and a biological information measurement support program capable of supporting efficient measurement of biological information.

Hereinafter, an embodiment of the present invention will be described with reference to the drawings.

Figure 1:
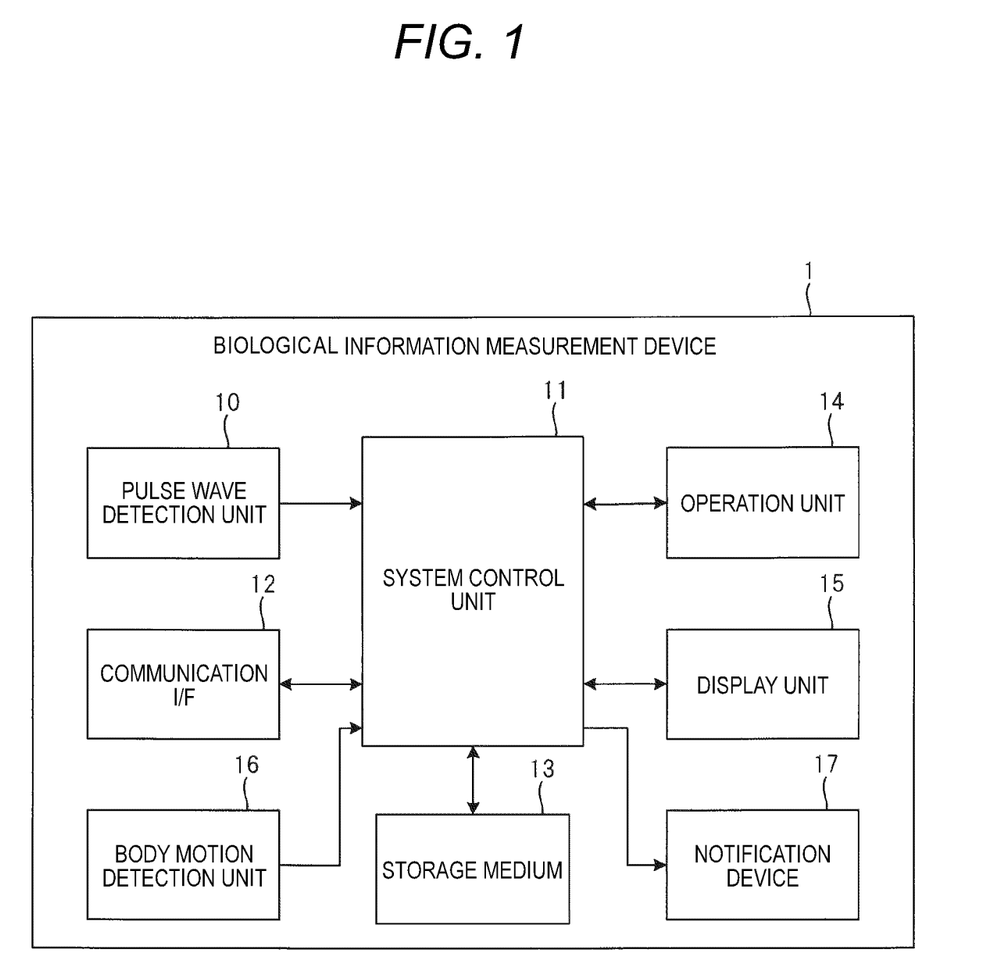
FIG. 1 depicts an internal hardware configuration of a biological information measurement device 1 for illustrating an embodiment of the present invention.

FIG. 1 depicts an internal hardware configuration of a biological information measurement device 1 for illustrating an embodiment of the present invention. The biological information measurement device 1 is used to monitor bedtime biological information of a measurement subject, for example.

The biological information measurement device 1 is to measure and store biological information such as blood pressure information, pulse information, vascular property information, heartbeat information and the like in a storage medium 13. The blood pressure information includes, for example a systolic arterial pressure, a diastolic pressure, an average blood pressure and the like. The pulse information includes, for example, a pulse rate and the like. The heartbeat information includes, for example, a heart rate and the like. The vascular property information includes, for example, AI (Augmentation Index), PTT (Pulse Transit Time) and the like.

The biological information measurement device 1 includes a pulse wave detection unit 10, a system control unit 11 configured to collectively control the entire device, a communication interface (I/F) 12, a storage medium 13, an operation unit 14, a display unit 15, a body motion detection unit 16 and a notification device 17.

The pulse wave detection unit 10 is configured to detect a pulse wave to occur every one pulse from a living body part (for example, a wrist) of the measurement subject and to input the detected pulse wave in the system control unit 11. The pulse wave detection unit 10 is configured to detect a pressure pulse wave as the pulse wave by a tonometry method, for example. The pulse wave detection unit 10 may be configured to detect a volume pulse wave as the pulse wave. The pulse wave detection unit 10 may be configured to detect the pulse wave by reflected light from the artery obtained by irradiating light to the artery.

When the wave detection unit 10 is configured to detect the pulse wave by the tonometry method, the pulse wave detection unit 10 includes a pressure sensor and a pressing part such as an air bag configured to press the pressure sensor to a body surface. The pulse wave detection unit 10 is configured to detect the pulse wave based on a signal that is to be detected by the pressure sensor in a state where the pressure sensor is pressed to the body surface with a predetermined pressing force by the pressing part.

The system control unit 11 includes a processor, as a main body, and a ROM (Read Only Memory) in which a program and the like to be executed by the processor are stored, a RAM (Random Access Memory) as a work memory, and the like.

The system control unit 11 is configured to calculate biological information based on a pulse wave continuously detected by the pulse wave detection unit 10, and to store the calculated biological information in the storage medium 13, in association with information of a date on which the pulse wave is detected and information of time at which the pulse wave is detected.

The communication I/F 12 is an interface for wired or wireless connection with other electronic devices (for example, a hospital terminal equipped in a hospital or an electronic device such as a smart phone carried by the measurement subject wearing the biological information measurement device 1).

In the storage medium 13, a variety of data such as the biological information calculated by the system control unit 11 is stored. The storage medium 13 is configured by a flash memory, a hard disk and the like, for example. The storage medium 13 may be a portable type to be detachably mounted to the biological information measurement device 1.

The operation unit 14 is an interface for inputting an instruction signal to the system control unit 11, and is configured by buttons, a touch panel and the like for instructing start or end of diverse operations including measurement of the biological information.

The display unit 15 is to display a variety of information such as the measured biological information, and is configured by a liquid crystal display device or the like, for example.

The body motion detection unit 16 is configured to detect motion of the living body part on which the biological information measurement device 1 is worn, and to input body motion information corresponding to the motion to the system control unit 11. The body motion detection unit 16 is configured by a sensor such as an acceleration sensor, an angular velocity sensor and the like, and a signal processing unit configured to process a signal output from the sensor.

The notification device 17 is a device for performing notification to the measurement subject wearing the biological information measurement device 1, and includes a speaker configured to output a sound, a vibrator configured to vibrate the biological information measurement device 1, or the like.

Figure 2:
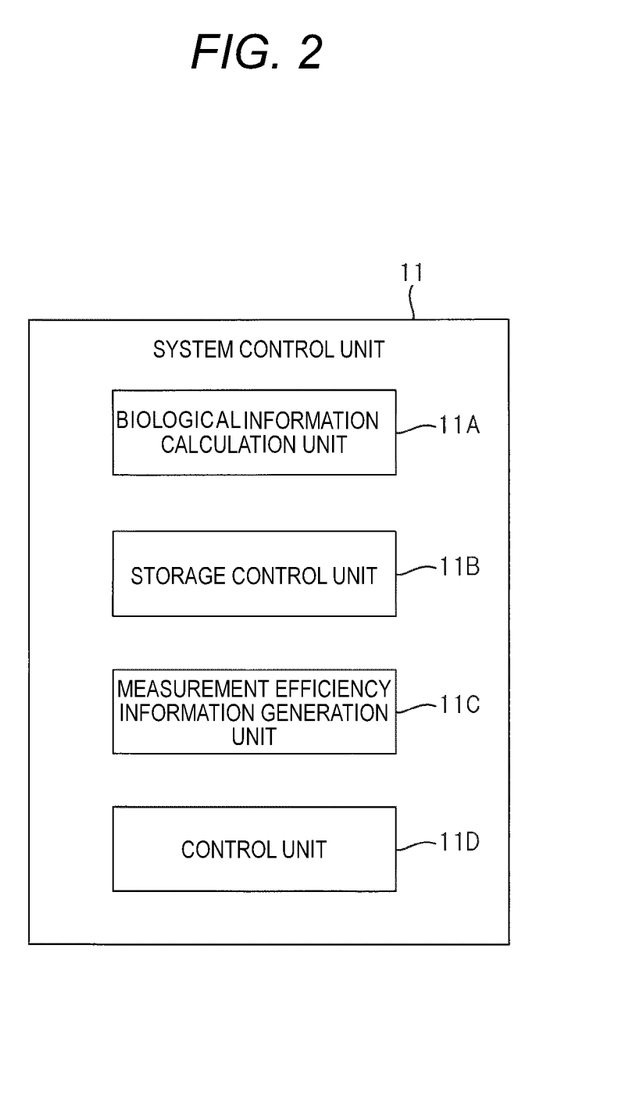
FIG. 2 is a functional block diagram of a system control unit 11 of the biological information measurement device 1 shown in FIG. 1.

FIG. 2 is a functional block diagram of the system control unit 11 of the biological information measurement device 1 shown in FIG. 1.

The system control unit 11 includes a biological information calculation unit 11A, a storage control unit 11B, a measurement efficiency information generation unit 11C and a control unit 11D.

The biological information calculation unit 11A, the storage control unit 11B, the measurement efficiency information generation unit 11C and the control unit 11D are configured as the processor executes the programs stored in the ROM. The programs include a biological information measurement support program.

The biological information calculation unit 11A is configured to calculate the biological information based on the pulse wave input from the pulse wave detection unit 10 by the well-known method. The biological information calculation unit 11A uses the pulse wave detected every one pulse, as the pulse wave of a calculation target of the biological information, but may set a pulse wave detected every other pulse or every multiple pulses, as the calculation target of the biological information.

The biological information calculation unit 11A is configured to store the calculated biological information in the storage medium 13, in association with the information of date and time at which the pulse wave used for the calculation of the biological information is detected. Thereby, in the storage medium 13, the biological information in a unit of one pulse is accumulatively stored.

The biological information calculation unit 11A is configured to calculate the biological information based on the pulse wave input from the pulse wave detection unit 10. However, when an input pulse wave does not satisfy a preset adoption condition, the biological information calculation unit does not calculate the biological information based on the pulse wave, and stores the information of date and time at which the pulse wave is detected in the storage medium 13, in association with measurement failure information indicating that the pulse wave does not satisfy the adoption condition.

Also, when the pulse wave input from the pulse wave detection unit 10 satisfies the adoption condition, the biological information calculation unit 11A calculates the biological information based on the pulse wave, and stores the information of date and time at which the pulse wave is detected and the calculated biological information in the storage medium 13, in association with measurement success information indicating that the pulse wave satisfies the adoption condition.

The adoption condition includes a first condition that the input pulse wave is a pulse wave detected during a body motion stable time period in which a motion amount of the wrist of the measurement subject based on the body motion information detected by the body motion detection unit 16 is smaller than a body motion threshold value, a second condition that a shape of the input pulse wave is a shape capable of calculating the biological information, and the like.

For example, when calculating the pulse rate, it is necessary to calculate time between peaks of the adjacent pulse waves or time between rising times of the adjacent pulse waves. However, when the input pulse wave has a shape incapable of specifying the peak, the rising time and the like, the corresponding pulse wave does not satisfy the adoption condition.

The biological information (the biological information stored with being associated with the measurement success information) calculated based on the pulse wave satisfying the adoption condition by the biological information calculation unit 11A is biological information of which reliability is equal to or higher than a threshold value.

In the meantime, when the first condition is used as the adoption condition, it may be possible to calculate the biological information based on the pulse wave not satisfying the adoption condition. To this end, in the case of the pulse wave not satisfying the first condition, the biological information calculation unit 11A may calculate the biological information based on the corresponding pulse wave, and store the calculated biological information and the information of date and time at which the pulse wave is detected in the storage medium 13, in association with the measurement failure information.

The storage control unit 11B is configured to store the pulse wave detected by the pulse wave detection unit 10 in the storage medium 13, in association with the information of date and time at which the pulse wave is detected.

Figure 3:
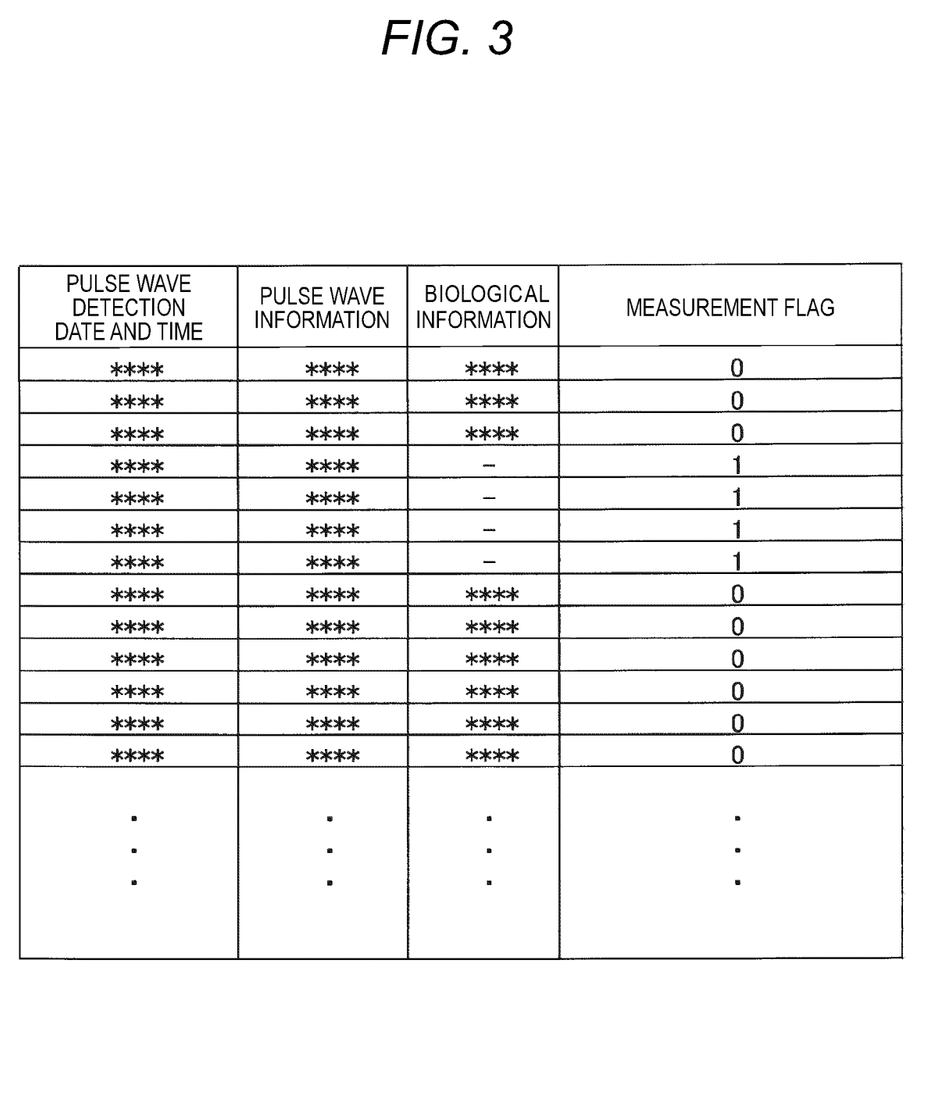
FIG. 3 depicts an example of a data structure of measured data that is to be stored in a storage medium 13 of the biological information measurement device 1 shown in FIG. 1.

FIG. 3 depicts an example of a data structure of measured data that is to be stored in the storage medium 13 of the biological information measurement device 1 shown in FIG. 1.

The measured data is data including pulse wave detection result information, which indicates a result of pulse wave detection processing executed by the pulse wave detection unit 10 after a measurement start instruction of the biological information is issued, and biological information calculation result information, which indicates a result of biological information calculation processing executed based on the pulse wave detected by the pulse wave detection processing.

When the measurement subject wears the biological information measurement device 1 and issues a measurement start instruction of the biological information, information ("pulse wave information" in FIG. 3) of the pulse wave detected during sleep of the measurement subject, biological information calculated based on the pulse wave, and a measurement flag (information of "1" or "0") indicating whether the pulse wave satisfies the adoption condition are stored in association with date and time ("pulse wave detection date and time" in FIG. 3) at which the pulse wave is detected, as shown in FIG. 3. The information of date and time of the pulse wave is treated as a detected pulse wave ID, too.

The measurement flag "1" is information configuring the measurement failure information and indicating that the pulse wave specified by the corresponding ID does not satisfy the adoption condition.

The measurement flag "0" is information configuring the measurement success information and indicating that the pulse wave specified by the corresponding ID satisfies the adoption condition (in other words, information indicating that the reliability of the biological information calculated based on the pulse wave specified by the corresponding ID is equal to or higher than a threshold value).

The pulse wave detection date and time and the pulse wave information corresponding to the pulse wave detection date and time shown in FIG. 3 configure the pulse wave detection result information indicative of a result of the pulse wave detection processing, respectively.

The pulse wave detection date and time, the biological information and the measurement flag shown in FIG. 3 configure the biological information calculation result information indicative of a calculation result of the biological information made by the biological information calculation unit 11A, respectively.

Returning to FIG. 2, the measurement efficiency information generation unit 11C is configured to generate information (hereinafter, referred to as 'measurement efficiency information') indicative of a measurement efficiency of the biological information included in the measured data, based on the measured data (FIG. 3) stored in the storage medium 13, whenever the measurement start instruction of the biological information is issued and the pulse wave is then detected or at predetermined periodic timing such as every several seconds.

The measurement efficiency of the biological information is an index indicating how the biological information having the reliability equal to or higher than the threshold value could be stored in the storage medium 13 without waste for a time period after the measurement start instruction of the biological information is issued to start the measurement operation (detection of the pulse wave and calculation and storing of the biological information based on the pulse wave).

The measurement efficiency information generation unit 11C is configured to generate, as the measurement efficiency information, a measurement success rate (%), which is a ratio of the measurement flag "0" to the total number of the pulse wave information included in the measured data stored in the storage medium 13 after the measurement start instruction of the biological information is issued, for example.

The measurement efficiency information generation unit 11C may be configured, as the measurement success rate (%), a ratio of a length of a cumulative time period (measurement success time period) of time periods, in which pulse waves becoming a calculation source of the biological information of which reliability stored in the storage medium 13 is equal to or higher than a threshold value (the biological information for which the measurement flag is set as "0") have been detected, to a length of a time period (measurement time period) from the issuance of the measurement start instruction of the biological information to the timing. The measurement success rate is information indicating that the larger a value thereof is, the higher the measurement efficiency is.

Alternatively, the measurement efficiency information generation unit 11C is configured to generate, as the measurement efficiency information, a measurement failure rate (%), which is a ratio of the measurement flag "1" to the total number of the pulse wave information included in the measured data stored in the storage medium 13 after the measurement start instruction of the biological information is issued.

The measurement efficiency information generation unit 11C may be configured, as the measurement failure rate (%), a ratio of a length of a cumulative time period (measurement failure time period) of time periods, in which pulse waves becoming a calculation source of the biological information of which reliability stored in the storage medium 13 is less than the threshold value (the biological information for which the measurement flag is set as "1") have been detected, to the length of the measurement time period. The measurement failure rate is information indicating that the larger a value thereof is, the lower the measurement efficiency is.

When the measurement efficiency information generated by the measurement efficiency information generation unit 11C satisfies a predetermined third condition, the control unit 11D performs a predetermined control.

The third condition is that the measurement efficiency based on the measurement efficiency information is lowered, and specifically, is that when the measurement efficiency information is the measurement success rate, the measurement success rate is equal to or less than a predetermined success threshold value (for example, 40% or the like).

The third condition is that when the measurement efficiency information is the measurement failure rate, the measurement failure rate is equal to or higher than a predetermined failure threshold value (for example, 60% or the like).

The control that is executed by the control unit 11D is to control the notification device 17 to make a notification to the measurement subject. When the notification device 17 is a speaker, the control unit 11D outputs a sound from the speaker for notification. When the notification device 17 is a vibrator, the control unit 11D vibrates the vibrator to vibrate the biological information measurement device 1 for notification.

Figure 4:
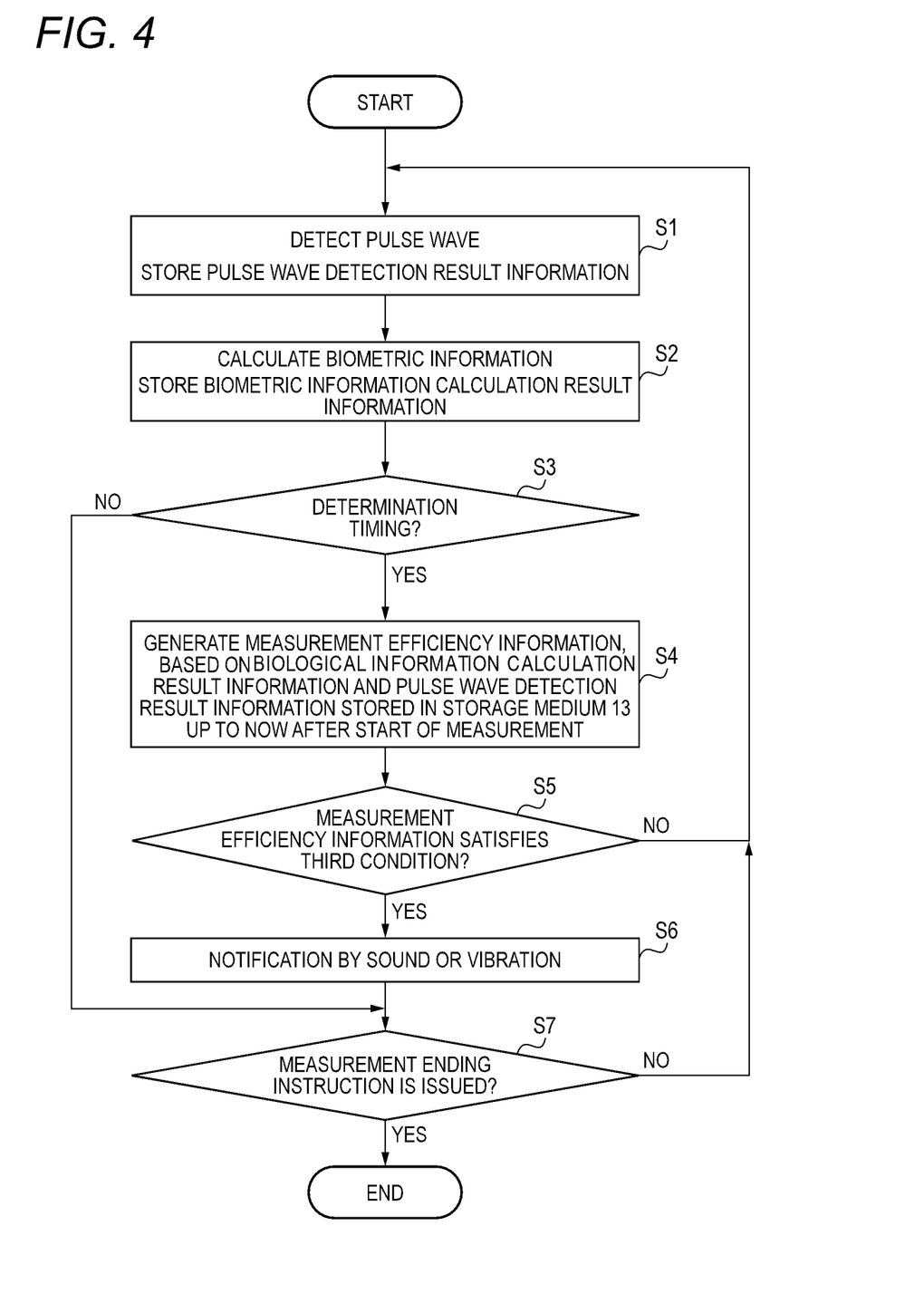
FIG. 4 is a flowchart depicting operations of the biological information measurement device 1 shown in FIG. 1.

FIG. 4 is a flowchart depicting operations of the biological information measurement device 1 shown in FIG. 1.

When the operation unit 14 is operated to issue a measurement start instruction of the biological information, the pulse wave detection unit 10 starts pulse wave detection processing. The pulse wave detected by the pulse wave detection processing is stored in the storage medium 13, in association with the information of date and time (step S1). When the pulse wave detection processing starts, the system control unit 11 executes processing of calculating and storing the biological information based on the pulse wave detected by the pulse wave detection unit 10 (step S2).

After starting the measurement of the biological information, the system control unit 11 determines whether it is a determination timing for determining the measurement efficiency. When it is determined that it is a determination timing (step S3: YES), the system control unit 11 executes processing of step S4, and when it is determined that it is not a determination timing (step S3: NO), the system control unit 11 executes processing of step S7.

In step S7, the system control unit 11 determines whether a measurement ending instruction of the biological information has been issued. When it is determined that the measurement ending instruction has not been issued (step S7: NO), the system control unit 11 returns the processing to step S1, and when it is determined that the measurement ending instruction has been issued (step S7: YES), the system control unit 11 stops the pulse wave detection of the pulse wave detection unit 10 to end the measurement operation.

In step S4, the system control unit 11 generates the measurement efficiency information, based on the biological information calculation result information and pulse wave detection result information included in the measured data stored in the storage medium 13 after the measurement start instruction of the biological information has been issued until the determination timing.

Then, the system control unit 11 determines whether the measurement efficiency information satisfies the third condition (step S5). When it is determined that the measurement efficiency information satisfies the third condition (step S5: YES), the system control unit 11 controls the notification device 17 to output a sound from the speaker or to vibrate the biological information measurement device 1 for notification to the measurement subject (step S6). After step S6, the processing of step S7 is executed.

By the processing of step S6, a message "The biological information has not been measured well. Please again wear the device." is output with the voice from the speaker, for example. The system control unit 11 may display a message for urging the user to again wear the biological information measurement device 1 on the display unit 15, together with the processing of step S6.

When it is determined that the measurement efficiency information does not satisfy the third condition (step S5: NO), the system control unit 11 returns the processing to step S1.

As described above, according to the biological information measurement device 1, when the measurement efficiency information satisfies the third condition, i.e., when the measurement efficiency of the biological information is low, the notification is made to the measurement subject by the sound or vibration. Therefore, the measurement subject can know that the biological information has not been measured well by the sound or vibration.

Therefore, when the measurement subject again wears the biological information measurement device 1 on the wrist in accordance with the notification, it is possible to change a contact state of the sensor, which is included in the pulse wave detection unit 10, with the wrist, and when the measurement subject again wears the biological information measurement device 1, it is possible to effectively measure the biological information. Thereby, it is possible to support the efficient measurement of the biological information.

In the meantime, the control that is to be performed by the control unit 11D when the measurement efficiency information satisfies the third condition is not limited to the sound or vibration notification.

For example, when the measurement efficiency information satisfies the third condition, the control unit 11D may stop the pulse wave detection processing of the pulse wave detection unit 10 to stop the measurement operation of the biological information.

Like this, when the measurement efficiency is low, the pulse wave detection processing is stopped, so that it is possible to prevent the measurement from being continuously executed as the measurement success rate is low and to prevent the useless measurement, thereby supporting the efficient measurement of the biological information.

In the case where the wave detection unit 10 is configured to detect the pulse wave by the tonometry method, when the measurement efficiency information satisfies the third condition, the control unit 11D may execute control of temporarily stopping the detection of the pulse wave by releasing a state in which the pressure sensor is pressed to the body surface by the pressing part included in the pulse wave detection unit 10, and then again pressing the pressure sensor to the body surface by the pressing part to thereby resume the detection of the pulse wave.

Like this, when the measurement efficiency is low, the control of returning the pressing force of the pressing part to an initial state and then increasing the pressing force to a predetermined value is executed to change the contact manner of the pressure sensor to the body surface, so that it is possible to improve the measurement efficiency, thereby supporting the efficient measurement of the biological information.

Also, when the measurement efficiency information satisfies the third condition, the control unit 11D may execute control of transmitting information (for example, information of date and time of the determination timing or a time zone including the determination timing), which indicates the determination timing at which the measurement efficiency information satisfies the third condition, from the communication I/F 12 to an electronic device such as a server equipped in a hospital and the like.

In this case, the measurement subject installs an application program in an electronic device such as a smart phone carried by the measurement subject. The control unit 11D of the biological information measurement device 1 transmits the information indicative of the determination timing to the electronic device. By a function of the application program, the smart phone transmits the information, which indicates the determination timing received from the biological information measurement device 1, to a server registered in advance. In this way, the information indicative of the timing at which the measurement efficiency is lowered to the electronic device different from the biological information measurement device 1, so that an administrator managing the electronic device can know what time zone the measurement subject could not measure the biological information well.

As the electronic device of the transmission destination to which the control unit 11D is to transmit the information indicative of the determination timing, an electronic device that is managed by a manufacturer of the biological information measurement device 1, an electronic device that is managed by a service provider providing a specific service to the measurement subject based on the measured data to be measured by the biological information measurement device 1, and the like may be registered, in addition to the electronic device that is managed by a healthcare professional.

When the electronic device that is managed by a healthcare professional is registered as the transmission destination, the healthcare professional can perceive a measurement situation of a patient and take measures for the patient, such as an advice on a measurement method. Thereby, it is possible to support the efficient measurement of the biological information.

When the electronic device that is managed by a manufacturer of the biological information measurement device 1 is registered as the transmission destination, the manufacturer can collect cases where the measurement efficiency is lowered, and utilize the same for product development.

When the electronic device that is managed by a service provider is registered as the transmission destination, the service provider can utilize the information for improvement on the service quality or development of the service.

When the measurement efficiency information is the measurement success rate, the third condition may be that the measurement success rate generated in step S4 monotonically decreases and is equal to or smaller than the success threshold value. When the measurement efficiency information is the measurement failure rate, the third condition may be that the measurement failure rate monotonically increases and is equal to or larger than the failure threshold value.

The description "the measurement efficiency information monotonically decreases" means that a state where a value obtained by subtracting the measurement efficiency information generated immediately before the latest measurement efficiency information from the latest measurement efficiency information generated in the processing of step S4 becomes equal to or smaller than a predetermined value continues at least two times or more.

The description "the measurement efficiency information monotonically increases" means that a state where a value obtained by subtracting the measurement efficiency information generated immediately before the latest measurement efficiency information from the latest measurement efficiency information generated in the processing of step S4 becomes equal to or larger than a predetermined value continues at least two times or more.

Like this, the continuous lowering of the measurement efficiency is added to the third condition, so that it is possible to prevent the notification from being made when the measurement efficiency is temporarily lowered due to rolling over of the measurement subject, for example. That is, it is possible to prevent the unnecessary control from being executed by the control unit 11D and to save the power.

In the above, the measurement efficiency information generation unit 11C of the system control unit 11 generates the measurement efficiency information, based on the pulse wave detection result information and biological information calculation result information stored for the time period from the issuance of the measurement start instruction of the biological information to the determination timing.

As a modified embodiment, the measurement efficiency information generation unit 11C classifies the pulse wave detection date and time of the measured data (FIG. 3) corresponding to one day and stored in the storage medium 13 into each time zone, at a timing at which the measurement ending instruction of the biological information is issued. The measurement efficiency information generation unit 11C generates the measurement efficiency information in each time zone, based on the pulse wave detection date and time belonging to each time zone and the pulse wave information, biological information and measurement flag corresponding to the pulse wave detection date and time, and stores the generated measurement efficiency information in the storage medium 13 in association with information indicative of each time zone and date information.

The measurement efficiency information generation unit 11C repetitively executes the above processing for the measured data corresponding to a plurality of days, and generates the measurement efficiency information in each time zone of one day, for the plurality of days and stores the same in the storage medium 13.

When the measurement efficiency information in each time zone of one day is generated for the plurality of days, the control unit 11D specifies time zones and dates in which the measurement efficiency based on the measurement efficiency information is equal to or less than an efficiency threshold value. When the measurement efficiency information satisfies the third condition, the measurement efficiency based on the measurement efficiency information becomes equal to or less than the efficiency threshold value. When there is an overlapping specific time zone, the control unit 11D notifies information, which indicates that the measurement efficiency of the biological information is low in the overlapping time zone, by using the notification device 17.

According to the above modified embodiment, when the measurement efficiency is lowered in the same time zone over the plurality of days, it is notified to the measurement subject. By this notification, it is possible to enable the measurement subject to recognize the time zone in which the measurement efficiency is lowered, and to urge the measurement subject to investigate a cause due to which the measurement efficiency is lowered. Thereafter, when the measurement subject investigates the cause and takes necessary measures, it is possible to improve the measurement efficiency.

The measurement efficiency information generation unit 11C preferably excludes the pulse wave detection result information and the biological information calculation result information, which are stored in the storage medium 13 up to a point of time after a predetermined time period elapses from the issuance of the measurement start instruction, of the measured data stored in the storage medium 13 after the issuance of the measurement start instruction from the information that is to be used for generation of the measurement efficiency information.

The measurement start instruction is input to the system control unit 11 by operating the operation unit 14. For example, when the biological information measurement device 1 is worn on the wrist, a noise due to the body motion may be superimposed on the pulse wave by a hand operation for operating the operation unit 14. When the measurement efficiency information is generated with the pulse wave having the noise superimposed thereon being included, the measurement efficiency may be lowered below an actual value.

For this reason, the pulse wave detected for a time period in which the noise is likely to be generated, such as an operating time period of the operation unit 14, and the biological information calculated based on the pulse wave are excluded from the information that is to be used for generation of the measurement efficiency information, so that it is possible to obtain the more correct measurement efficiency information.

When it is assumed that the biological information measurement device 1 is used during the sleep, the predetermined time is preferably time after the measurement start instruction has been issued until a change amount in the body motion of the measurement subject wearing the biological information measurement device 1 enters a predetermined range. That is, the measurement efficiency information generation unit 11C preferably excludes the pulse wave detection result information and the biological information calculation result information, which are stored in the storage medium 13 for the time period after the measurement start instruction has been issued until a change amount in the body motion of the measurement subject enters a predetermined range, of the measured data from the information that is to be used for generation of the measurement efficiency information.

Like this, the pulse wave generated due to the motion of the measurement subject during the sleep and the biological information calculated based on the pulse wave are excluded from the information that is to be used for generation of the measurement efficiency information, so that it is possible to obtain the more correct measurement efficiency information.

The biological information measurement support program is stored in a non-transitory storage medium from which a computer can read the program.

The "computer-readable storage medium" includes an optical medium such as a ROM and a CD-ROM (Compact Disc-ROM), a magnetic recording medium such as a memory card, and the like, for example. Also, the program may be provided by a downloading through a network.

The disclosed embodiments are exemplary in every respect and should not be construed as being limited. The scope of the present invention is defined in the claims, not in the above description, and includes all changes within the meaning and scope equivalent to the claims.

As described above, the specification discloses following items.

(1) A biological information measurement device including a pulse wave detection unit configured to continuously detect a pulse wave from a living body, a biological information calculation unit configured to calculate and store biological information based on the pulse wave detected by the pulse wave detection unit in a storage medium, a storage control unit configured to store, in the storage medium, pulse wave detection result information indicative of a result of pulse wave detection processing executed by the pulse wave detection unit so as to calculate the biological information, a measurement efficiency information generation unit configured to generate measurement efficiency information indicative of a measurement efficiency of the biological information stored in the storage medium, based on biological information calculation result information indicative of a calculation result of the biological information made by the biological information calculation unit and the pulse wave detection result information, and a control unit configured to, when the measurement efficiency information satisfies a predetermined condition, execute a predetermined control.

(2) The biological information measurement device according to the above (1), wherein the control is a control of stopping detection of the pulse wave by the pulse wave detection unit.

(3) The biological information measurement device according to the above (1), wherein the pulse wave detection unit includes a pressure sensor and a pressing part configured to press the pressure sensor to a body surface, and is configured to detect the pulse wave based on a signal that is to be detected by the pressure sensor in a state where the pressure sensor is pressed to the body surface with a predetermined pressing force by the pressing part, and wherein the control is a control of releasing a state in which the pressure sensor is pressed to the body surface by the pressing part, and then again pressing the pressure sensor to the body surface by the pressing part to thereby resume detection of the pulse wave.

(4) The biological information measurement device according to the above (1), wherein the control is a control of outputting a sound from a speaker or vibrating the biological information measurement device.

(5) The biological information measurement device according to the above (1), wherein the control is a control of transmitting information, which indicates a timing at which the measurement efficiency information satisfies the condition, to an external electronic device.

(6) The biological information measurement device according to one of the above (1) to (5), wherein when the measurement efficiency information is information indicating that the larger a value thereof is, the higher the measurement efficiency is, the condition is that the measurement efficiency information is equal to or smaller than a threshold value, and wherein when the measurement efficiency information is information indicating that the larger a value thereof is, the lower the measurement efficiency is, the condition is that the measurement efficiency information is equal to or larger than a threshold value.

(7) The biological information measurement device according to one of the above (1) to (5), wherein when the measurement efficiency information is information indicating that the larger a value thereof is, the higher the measurement efficiency is, the condition is that the measurement efficiency information monotonically decreases and is equal to or smaller than a threshold value, and wherein when the measurement efficiency information is information indicating that the larger a value thereof is, the lower the measurement efficiency is, the condition is that the measurement efficiency information monotonically increases and is equal to or larger than a threshold value.

(8) The biological information measurement device according to the above (1), wherein the measurement efficiency information generation unit is configured to generate the measurement efficiency information, which indicates the measurement efficiency of the biological information calculated and stored by the biological information calculation unit in each time zone of one day, and wherein when there is an overlapping time zone in which the measurement efficiency based on the measurement efficiency information is equal to or less than an efficiency threshold value, the control unit executes the control of notifying information indicating that the measurement efficiency of the biological information is low in the overlapping time zone.

(9) The biological information measurement device according to one of the above (1) to (8), wherein the measurement efficiency information generation unit is configured to exclude information indicative of a detection result of the pulse waves detected up to a point of time after a predetermined time period elapses from issuance of a measurement start instruction of the biological information and information indicative of a calculation result of the biological information calculated based on the pulse waves from information that is to be used for generation of the measurement efficiency information.

(10) The biological information measurement device according to one of the above (1) to (8), further including a body motion detection unit configured to detect body motion of the measurement subject, wherein the measurement efficiency information generation unit is configured to exclude information, which indicates a detection result of the pulse waves detected for a time period after a measurement start instruction of the biological information is issued until a change amount in the body motion of the measurement subject enters a predetermined range, and information indicative of a calculation result of the biological information calculated based on the pulse waves from information that is to be used for generation of the measurement efficiency information.

(11) A biological information measurement support method including a biological information calculation step of calculating biological information based on a pulse wave detected by a pulse wave detection unit configured to continuously detect the pulse wave from a living body and storing, as information indicative of a calculation result of the biological information, biological information calculation result information including at least the biological information in a storage medium, a storage control step of storing, in the storage medium, pulse wave detection result information indicative of a result of pulse wave detection processing executed by the pulse wave detection unit so as to calculate the biological information to be included in the biological information calculation result information, a measurement efficiency information generation step of generating measurement efficiency information indicative of a measurement efficiency of the biological information based on the biological information calculation result information and the pulse wave detection result information, and a control step of, when the measurement efficiency information satisfies a predetermined condition, executing a predetermined control.

(12) A biological information measurement support program of the present invention configured to enable a computer to execute a biological information calculation step of calculating biological information based on a pulse wave detected by a pulse wave detection unit configured to continuously detect the pulse wave from a living body and storing, as information indicative of a calculation result of the biological information, biological information calculation result information including at least the biological information in a storage medium, a storage control step of storing, in the storage medium, pulse wave detection result information indicative of a result of pulse wave detection processing executed by the pulse wave detection unit so as to calculate the biological information to be included in the biological information calculation result information, a measurement efficiency information generation step of generating measurement efficiency information indicative of a measurement efficiency of the biological information based on the biological information calculation result information and the pulse wave detection result information, and a control step of, when the measurement efficiency information satisfies a predetermined condition, executing a predetermined control.

According to the present invention, it is possible to provide the biological information measurement device, the biological information measurement support method and the biological information measurement support program capable of supporting the efficient measurement of the biological information.

The present invention can be conveniently and effectively used for a portable blood pressure meter, particularly.

Although the present invention has been described with reference to the specific embodiment, the present invention is not limited to the embodiments and can be diversely changed without departing from the disclosed technical spirit of the present invention.

What is claimed is:

1. A biological information measurement device comprising:
   a pulse wave detector configured to continuously detect a pulse wave from a living body;
   a biological information calculation unit configured to calculate and store biological information based on the pulse wave detected by the pulse wave detector in a storage medium;
   a storage control unit configured to store, in the storage medium, pulse wave detection result information indicative of a result of pulse wave detection processing executed by the pulse wave detector to calculate the biological information;
   a measurement efficiency information generation unit configured to generate measurement efficiency information indicative of a measurement efficiency of the biological information stored in the storage medium, based on biological information calculation result information indicative of a calculation result of the biological information made by the biological information calculation unit and the pulse wave detection result information; and
   a control unit configured to, when the measurement efficiency information satisfies a predetermined condition, execute a predetermined control,
   wherein when the measurement efficiency is measured as a success rate, the measurement efficiency information is information indicating that a larger a value thereof is, a higher the measurement efficiency is, the predetermined condition is that a state where a value obtained by subtracting the measurement efficiency information generated immediately before the latest measurement efficiency information from the latest measurement efficiency information becomes equal to or smaller than a predetermined value continues at least two times or more, and that the measurement efficiency information is equal to or smaller than a threshold value, and
   wherein when the measurement efficiency is measured as a failure rate, the measurement efficiency information is information indicating that a larger a value thereof is, a lower the measurement efficiency is, the predetermined condition is that a state where a value obtained by subtracting the measurement efficiency information generated immediately before the latest measurement efficiency information from the latest measurement efficiency information becomes equal to or larger than a predetermined value continues at least two times or more, and that the measurement efficiency information is equal to or larger than a threshold value.

2. The biological information measurement device according to claim 1, the predetermined control is a control of stopping a detection of the pulse wave by the pulse wave detector.

3. The biological information measurement device according to claim 1, wherein the pulse wave detector includes a pressure sensor and a pressing part configured to press the pressure sensor to a body surface, and is configured to detect the pulse wave based on a signal that is to be detected by the pressure sensor in a state where the pressure sensor is pressed to the body surface with a predetermined pressing force by the pressing part, and
   wherein the predetermined control is a control of releasing a state in which the pressure sensor is pressed to the body surface by the pressing part, and then again pressing the pressure sensor to the body surface by the pressing part to thereby resume the detection of the pulse wave.

4. The biological information measurement device according to claim 1, wherein the predetermined control is a control of outputting a sound from a speaker or vibrating the biological information measurement device.

5. The biological information measurement device according to claim 1, wherein the predetermined control is a control of transmitting information, which indicates a timing at which the measurement efficiency information satisfies the predetermined condition, to an external electronic device.

6. The biological information measurement device according to claim 1, wherein the measurement efficiency information generation unit is configured to exclude, from information that is to be used for generation of the measurement efficiency information, information indicative of a detection result of the pulse waves detected up to a point of time after a predetermined time period elapses from issuance of a measurement start instruction of the biological information and information indicative of a calculation result of the biological information calculated based on the pulse waves.

7. The biological information measurement device according to claim 1, further comprising:
   a body motion detector configured to detect body motion of the living body, wherein the measurement efficiency information generation unit is configured to exclude, from information that is to be used for generation of the measurement efficiency information, information which indicates a detection result of the pulse waves detected for a time period after a measurement start instruction of the biological information is issued until a change amount in the body motion of the living body enters a predetermined range, and information indicative of a calculation result of the biological information calculated based on the pulse waves.

8. A biological information measurement device comprising:
a pulse wave detector configured to continuously detect a pulse wave from a living body;
a biological information calculation unit configured to calculate and store biological information based on the pulse wave detected by the pulse wave detector in a storage medium;
a storage control unit configured to store, in the storage medium, pulse wave detection result information indicative of a result of pulse wave detection processing executed by the pulse wave detector to calculate the biological information;
a measurement efficiency information generation unit configured to generate measurement efficiency information indicative of a measurement efficiency of the biological information stored in the storage medium, based on biological information calculation result information indicative of a calculation result of the biological information made by the biological information calculation unit and the pulse wave detection result information; and
a control unit configured to, when the measurement efficiency information satisfies a predetermined condition, execute a predetermined control,
wherein the measurement efficiency information generation unit is configured to generate the measurement efficiency information, which indicates the measurement efficiency of the biological information calculated and stored by the biological information calculation unit for each of a plurality of time zones in each of a plurality of days, and
wherein when there is a same time zone of the plurality of time zones over the plurality of days in which the measurement efficiency based on the measurement efficiency information is equal to or less than an efficiency threshold value, the control unit specifies time zones in which the measurement efficiency is low and executes the predetermined control of notifying information indicating that the measurement efficiency of the biological information is low in the same time zone.

9. A biological information measurement support method comprising:
a biological information calculation step of calculating biological information based on a pulse wave detected by a pulse wave detector configured to continuously detect the pulse wave from a living body and storing, as information indicative of a calculation result of the biological information, biological information calculation result information including at least the biological information in a storage medium;
a storage control step of storing, in the storage medium, pulse wave detection result information indicative of a result of pulse wave detection processing executed by the pulse wave detector to calculate the biological information to be included in the biological information calculation result information;
a measurement efficiency information generation step of generating measurement efficiency information indicative of a measurement efficiency of the biological information based on the biological information calculation result information and the pulse wave detection result information; and
a control step of, when the measurement efficiency information satisfies a predetermined condition, executing a predetermined control,
wherein when the measurement efficiency is measured as a success rate, the measurement efficiency information is information indicating that a larger a value thereof is, a higher the measurement efficiency is, the predetermined condition is that a state where a value obtained by subtracting the measurement efficiency information generated immediately before the latest measurement efficiency information from the latest measurement efficiency information becomes equal to or smaller than a predetermined value continues at least two times or more, and that the measurement efficiency information is equal to or smaller than a threshold value, and
wherein when the measurement efficiency is measured as a failure rate, the measurement efficiency information is information indicating that a larger a value thereof is, a lower the measurement efficiency is, the predetermined condition is that a state where a value obtained by subtracting the measurement efficiency information generated immediately before the latest measurement efficiency information from the latest measurement efficiency information becomes equal to or larger than a predetermined value continues at least two times or more, and that the measurement efficiency information is equal to or larger than a threshold value.

10. A biological information measurement support method comprising:
a biological information calculation step of calculating biological information based on a pulse wave detected by a pulse wave detector configured to continuously detect the pulse wave from a living body and storing, as information indicative of a calculation result of the biological information, biological information calculation result information including at least the biological information in a storage medium;
a storage control step of storing, in the storage medium, pulse wave detection result information indicative of a result of pulse wave detection processing executed by the pulse wave detector to calculate the biological information to be included in the biological information calculation result information;
a measurement efficiency information generation step of generating measurement efficiency information indicative of a measurement efficiency of the biological information based on the biological information calculation result information and the pulse wave detection result information; and
a control step of, when the measurement efficiency information satisfies a predetermined condition, executing a predetermined control,
wherein in the measurement efficiency information generation step, the measurement efficiency information, which indicates the measurement efficiency of the biological information calculated and stored in the storage medium for each of a plurality of time zones in each of a plurality of days, is generated, and wherein in the control step, when there is a same time zone of the plurality of time zones over the plurality of days in which the measurement efficiency based on the measurement efficiency information is equal to or less than an efficiency threshold value, time zones in which the measurement efficiency is low are specified and the predetermined control of notifying information indicating that the measurement efficiency of the biological information is low in the same time zone is executed.

11. A non-transitory computer-readable storage medium, which stores a biological information measurement support program configured to enable a computer to execute a biological information measurement support method comprising:
- a biological information calculation step of calculating biological information based on a pulse wave detected by a pulse wave detector configured to continuously detect the pulse wave from a living body and storing, as information indicative of a calculation result of the biological information, biological information calculation result information including at least the biological information in a storage medium;
- a storage control step of storing, in the storage medium, pulse wave detection result information indicative of a result of pulse wave detection processing executed by the pulse wave detector to calculate the biological information to be included in the biological information calculation result information;
- a measurement efficiency information generation step of generating measurement efficiency information indicative of a measurement efficiency of the biological information based on the biological information calculation result information and the pulse wave detection result information; and
- a control step of, when the measurement efficiency information satisfies a predetermined condition, executing a predetermined control,
- wherein when the measurement efficiency is measured as a success rate, the measurement efficiency information is information indicating that a larger a value thereof is, a higher the measurement efficiency is, the predetermined condition is that a state where a value obtained by subtracting the measurement efficiency information generated immediately before the latest measurement efficiency information from the latest measurement efficiency information becomes equal to or smaller than a predetermined value continues at least two times or more, and that the measurement efficiency information is equal to or smaller than a threshold value, and
- wherein when the measurement efficiency is measured as a failure rate, the measurement efficiency information is information indicating that a larger a value thereof is, a lower the measurement efficiency is, the predetermined condition is that a state where a value obtained by subtracting the measurement efficiency information generated immediately before the latest measurement efficiency information from the latest measurement efficiency information becomes equal to or larger than a predetermined value continues at least two times or more, and that the measurement efficiency information is equal to or larger than a threshold value.

12. A non-transitory computer-readable storage medium, which stores a biological information measurement support program configured to enable a computer to execute a biological information measurement support method comprising:
- a biological information calculation step of calculating biological information based on a pulse wave detected by a pulse wave detector configured to continuously detect the pulse wave from a living body and storing, as information indicative of a calculation result of the biological information, biological information calculation result information including at least the biological information in a storage medium;
- a storage control step of storing, in the storage medium, pulse wave detection result information indicative of a result of pulse wave detection processing executed by the pulse wave detector to calculate the biological information to be included in the biological information calculation result information;
- a measurement efficiency information generation step of generating measurement efficiency information indicative of a measurement efficiency of the biological information based on the biological information calculation result information and the pulse wave detection result information; and
- a control step of, when the measurement efficiency information satisfies a predetermined condition, executing a predetermined control,
- wherein in the measurement efficiency information generation step, the measurement efficiency information, which indicates the measurement efficiency of the biological information calculated and stored in the storage medium for each of a plurality of time zones in each of a plurality of days, is generated, and
- wherein in the control step, when there is a same time zone of the plurality of time zones over the plurality of days in which the measurement efficiency based on the measurement efficiency information is equal to or less than an efficiency threshold value, time zones in which the measurement efficiency is low are specified and the predetermined control of notifying information indicating that the measurement efficiency of the biological information is low in the same time zone is executed.

* * * * *